United States Patent [19]

Hsieh et al.

[11] Patent Number: 5,225,980

[45] Date of Patent: * Jul. 6, 1993

[54] REDUCTION OF IMAGE ARTIFACTS FROM SUPPORT STRUCTURES IN TOMOGRAPHIC IMAGING

[75] Inventors: Jiang Hsieh, Waukesha; William K. Braymer, Muskego, both of Wis.

[73] Assignee: General Electric Company, Milwaukee, Wis.

[ * ] Notice: The portion of the term of this patent subsequent to Nov. 17, 2009 has been disclaimed.

[21] Appl. No.: 799,240

[22] Filed: Nov. 27, 1991

[51] Int. Cl.⁵ ............................................. G06F 15/42
[52] U.S. Cl. ..................... 364/413.14; 364/413.13; 364/413.16; 364/413.18
[58] Field of Search ................. 364/413.14, 413.13, 364/413.16, 413.18

[56] References Cited

U.S. PATENT DOCUMENTS 4,550,371 10/1985 Glover et al. ..................... 364/414
4,590,558 5/1986 Glover et al. ..................... 364/414
4,606,004 8/1986 Crawford et al. ................... 364/414

Primary Examiner—Robert A. Weinhardt
Assistant Examiner—Gita D. Shingala
Attorney, Agent, or Firm—Quarles & Brady

[57] ABSTRACT

An apparatus for reducing image artifacts caused by over-ranging or clipping of the data collected in a tomographic scan using a patient support, models the density profile of the patient support with a polynomial. Coefficients of the polynomial are stored in a look-up table according to gantry angle and used to estimate the over-range data. The estimated data is blended with the in-range data by convolving an over-range mask indicating which data is in-range and which data is over-range with a box car convolution kernel which produces a trapezoidal weighting mask. This weighting mask is multiplied by the estimated data and then summed to the in-range data to correct for the over-range portions of the data collected.

8 Claims, 7 Drawing Sheets

FIG. (b)

REDUCTION OF IMAGE ARTIFACTS FROM SUPPORT STRUCTURES IN TOMOGRAPHIC IMAGING

BACKGROUND OF THE INVENTION

This invention relates to tomographic imaging systems, such as x-ray computed tomography. More specifically, the invention relates to a method for reducing image artifacts caused by structures used to support an imaged object.

Tomographic imaging systems, as considered herein, are imaging systems which produce a tomographic or "slice" picture of an object such as the human body. Such tomographic systems collect a series of "projections" at various angles around the body, each projection made up of measurements of radiation emitted from the body. The radiation may be that transmitted through the body by an external radiation source, such as an x-ray tube, as in x-ray computed tomography ("CT") or the radiation may be that emitted from the body from internally placed radio-pharmaceutical isotopes, e.g. $T_c^{99}$ used in Single Photon Emission Computed Tomography (SPECT).

In an x-ray CT machine, an x-ray source is collimated to form a planar x-ray beam within an x-y plane of a Cartesian coordinate system. The beam is transmitted through the imaged body and received by a generally linear detector array also within this x-y plane.

The detector array is comprised of a plurality of adjacent detector elements each receiving radiation along a single "ray" from the focal spot of the x-ray source to that detector element. Each detector element produces a signal indicating the attenuation of the x-ray beam along that ray by the imaged body. The detector elements, the signal from each detector element, and the ray of the fan beam are all generally referred to as a "channel" of the projection, any ambiguity generally being resolved from the context of the use.

In one common embodiment, the planar x-ray beam is a "fan beam" radiating from a focal spot and the detector array has its elements organized in an arc of constant radius about the focal spot. The x-ray source and detector array may be rotated on a gantry around the imaged object so that the fan beam intersects the imaged object at different angles.

A number of projections are acquired at different gantry angles to form a tomographic projection set. The acquired projection set is typically stored in numerical form and may be "reconstructed" by mathematical techniques to yield a slice image. The reconstructed images may be displayed on a conventional CRT tube or may be converted to a film record by means of a computer controlled camera.

The natural evolution of x-ray CT has led to the development of higher powered x-ray sources. Such x-ray sources produce increased x-ray flux which is desirable for two reasons: First, increased flux improves the signal-to-noise ratio in the resulting image, for example, by minimizing the effect of noise. Second, increased flux permits the acquisition of the projection set during a shortened scanning time. Decreasing the scanning time improves patient comfort and helps minimize image artifacts caused by patient motion.

The use of increased x-ray power in an x-ray CT system creates the potential of overwhelming the system's detector signal chain. In particular, the analog-to-digital converter ("ADC") associated with the CT system's data acquisition system ("DAS") may be driven over its range. Such an over-range condition artificially limits the signal from any over-range channel to the maximum value of the ADC and causes the data of these channels to be effectively lost.

For the case of a patient scanned by a CT system, the over-range channels will typically be those channels which receive the peripheral rays of the fan beam, e.g. those near the outer edges of the patient and beyond. These areas may include support structures such as the patient table or a headholder and the loss of the channel data for these structures. Although it is relatively unimportant to produce accurate images of the support structure, incomplete data in this area will cause artifacts throughout the entire reconstructed image. This spreading of the effects of locally erroneous projection data is caused by the frequency domain filtering implicit in the image reconstruction process.

The problem of over-range channels is similar to the problem created by the truncation of projections when the imaged object extends outside of the fan beam and detector range. Such truncation may occur, for example, when the patient's arms are outside of the fan beam for some projections and in the fan beam for other projections.

U.S. Pat. No. 4,550,371, incorporated by-reference and assigned to the same assignee as the present application, provides a means for correcting a truncated projection by calculating the moments of all projections. Unfortunately, this method relies on the assumption that the majority of the projections are not truncated, an assumption which does not hold, in general, for projections having over-range channels.

One proposed method of correcting for the effect of over-range channels involves independently measuring the thickness of the imaged object along the rays associated with the over-range channels and substituting an attenuation value for those rays based on assumption of constant density of the imaged object along those rays. Although some success has been achieved with this approach, the requirement that the thickness of the body be measured independently is cumbersome and commercially impractical. Further, such measurements, based on simple models of the body being imaged do not take into account the complex attenuations caused by proximate patient supporting structure.

Ideally, any system for correcting for erroneous projection data caused by over-ranging should operate quickly enough so as not to significantly delay the production of tomographic images from the projection set. Preferably, the correction system should allow correction to begin as the projections are being acquired and should be susceptible to parallel processing in an array processor or the like, such processors as are commonly used for the reconstruction of tomographic images.

SUMMARY OF THE INVENTION

The present invention provides a means for correcting over-range data which results in the truncation of projections, specifically where the truncated data includes portions of a patient support structure or the like. The means requires as an input only the projection data from the projection being corrected and may be performed in parallel on the data processing hardware typically associated with tomographic systems.

Specifically, the channels of the projection data are received by a threshold detector which identifies them as in-range channels or over-range channels based on the maximum value associated with the data acquisition system. A model generator, programmed with the characteristics of the patient support, produces estimated over-range channels for the patient support. A combiner receives the estimated over-range channels and combines them with the in-range channels prior to the projection set being reconstructed into an image.

It is one object of the invention to provide an accurate estimation of the values of the over-range channels in a projection set without the need to scan the data of the other projections of that set. The model of the patient support uses gantry angle to deduce the contribution of the patient support to the present projection.

The model of the patient support may employ a function generator which receives a set of coefficients based on gantry angle to model the patient support by means of a polynomial. The polynomial may employ a piece-wise Gaussian basis function.

Thus, it is another object of the invention to provide an accurate model of the projections of a complex patient support without the need to store extremely large amounts of data such as that which would be required to store the actual projections of the patient support. The use of a piece-wise Gaussian function as the basis function for the polynomial allows the patient support to be adequately characterized with as few as six coefficients per gantry angle.

The combiner may comprise a mask generator for generating a binary over-range mask indicating which channels are over-range and which channels are in-range. A box car generator may be used to produce a convolution kernel which may be convolved with the mask generator signal to produce a convolved signal. The estimated over-range channels may be multiplied by the convolved signal and summed with the in-range channels to effect the combination. The convolved signal may be the convolved over-range mask and kernel clipped and scaled by predetermined value to a control the space between the estimated over-range channels and the in-range channels.

Thus, it is another object of the invention to provide a correction circuit suitable for implementation in parallel on an array processor or the like. The operations of convolution, multiplication, clipping and scaling are all readily performed in parallel as required by such processors.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

DETAILED DESCRIPTION OF THE PREFERRED EMBODIMENT

CT System Hardware

Figure 1A:
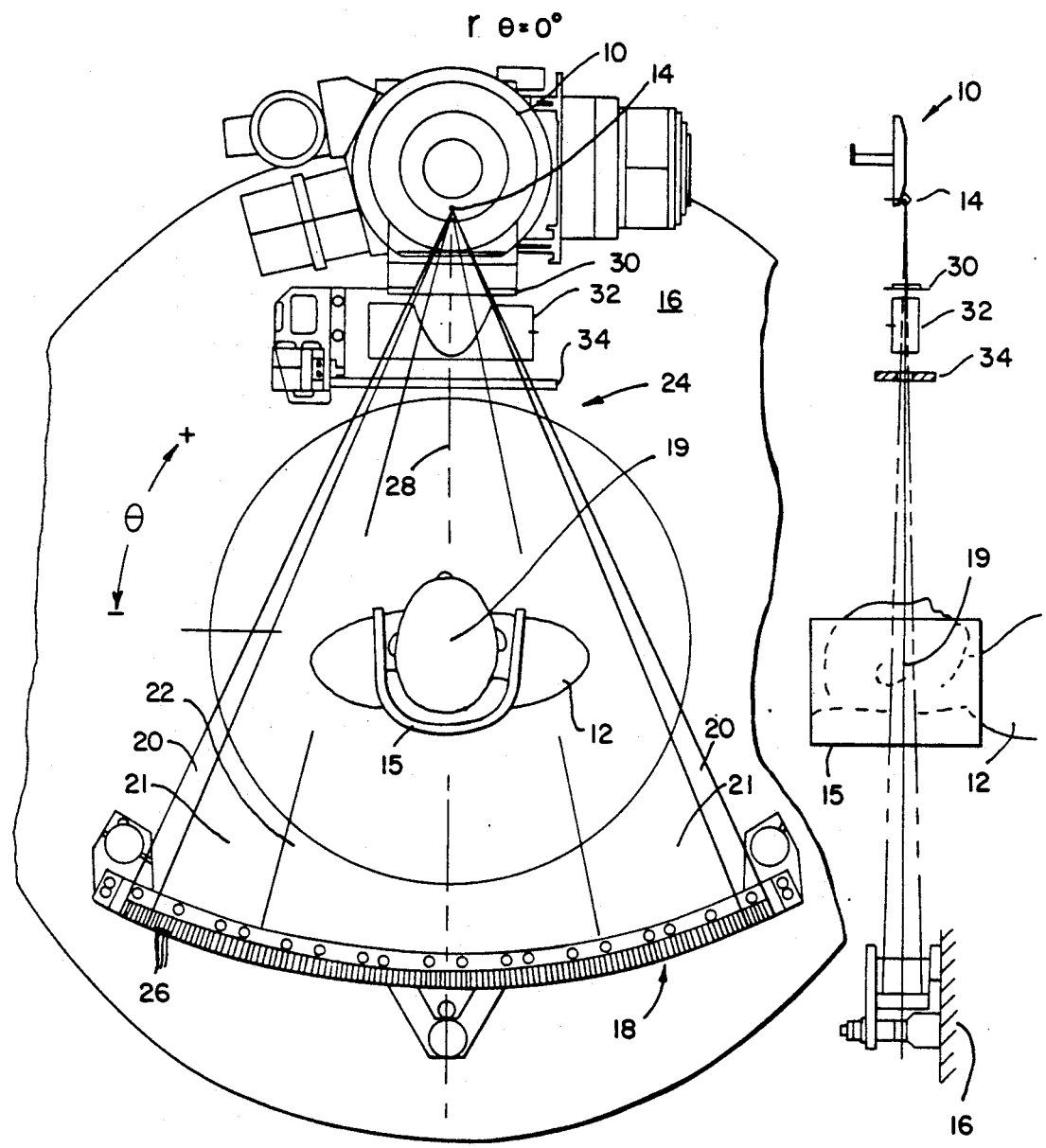
FIGS. 1($a$) and ($b$) are front and side views, in elevation, of a CT gantry showing the relative positions of an x-ray source, detector array and fan beam about a patient's head held within a headholder.

Referring to FIG. 1, a CT gantry 16, representative of that used with a "third generation" CT scanner, holds an x-ray source 10 producing a fan beam of x-rays 24. The fan beam 24 is directed through a patient 12, positioned near a center 19 of the gantry 16, to be received by a detector array 18 also attached to the gantry 16. The patient's head is supported by a headholder 15, the latter producing a small but significant attenuation of the x-rays of the fan beam 24.

The gantry 16 rotates within an x-y plane of a Cartesian coordinate system, termed the imaging plane, which is generally the same plane as that of the fan beam 24.

The detector array 18 is comprised of a number of detector elements or "channels" 26 positioned adjacent to each other within the imaging plane to subtend the fan beam 24. The channels 26 receive and detect radiation passing from the x-ray source 10, to produce a plurality of channel signals each associated with a particular channel 26. At a given orientation of gantry 16 about patient 12, signals for approximately 800 channels may be acquired, representing a detailed picture of the line integral of the attenuation of the fan beam 24 by the patient 12 at that angle. A gantry angle of zero is defined as that angle where a principle ray 28, centered in the fan beam 24, is directed vertically downward from the x-rays source 10.

The x-rays of the fan beam 24, immediately after leaving x-rays source 10 and prior to being received by the detector array 18, are filtered by a spectral filter 30 which filters out the lower energy x-rays from the fan beam 24. The fan beam 24 then passes through a bow tie filter 32 having a profile that produces an attenuation in the fan beam 24 complementing that which would be produced by a cylinder of water placed at the center 19 of the gantry 16. The purpose of the bow tie filter 32 is to reduce the range of intensity values received by the detector channels 26 for a typical patient 12 and hence to allow for an increase in sensitivity of the detector array 18 and its associated circuitry. This increased sensitivity also, however, increases the chance of a channel being over-range when the patient 12 differs significantly from the water cylinder model.

The bow tie filter 32 is followed by an aperture 34 which forms fan beam 24 and may be used to correct the position of the fan beam 24 with respect to the surface of the detector array 18 as described generally in U.S. Pat. No. 5,054,041 issued to the same assignee as that of the present application and incorporated herein by reference.

For a given patient 12, the channels 26 may be roughly divided into three groups: reference, over-range, and in-range. Reference channels 20 of the detector array 18 are those intended not to be occluded by the patient 12 or headholder 15 and may serve the function of calibrating the projection data for variations in the x-ray flux from x-ray source 10, and serve further to permit automatic alignment of the fan beam 24 on the detector array 18. Over-range channels 21 of the detector array 18 are those channels within a given projection which, although possibly occluded by the imaged object 12, generally receive x-rays having so little attenuation that the ADC, used to digitize the signals of these channels, is over-ranged. This over-ranging will be described further below. And finally, in-range channels 22 of the detector array 18, frequently but not necessarily near the center of the fan beam 24, are those in a given projection which are sufficiently attenuated by the imaged object 12 so as not to over-range the ADC used to digitize the signals from these channels.

In general, some over-range channels 21 will be present for substantially all of the projections taken of a convex patient 12 subtending less than the entire fan beam.

Figure 2:
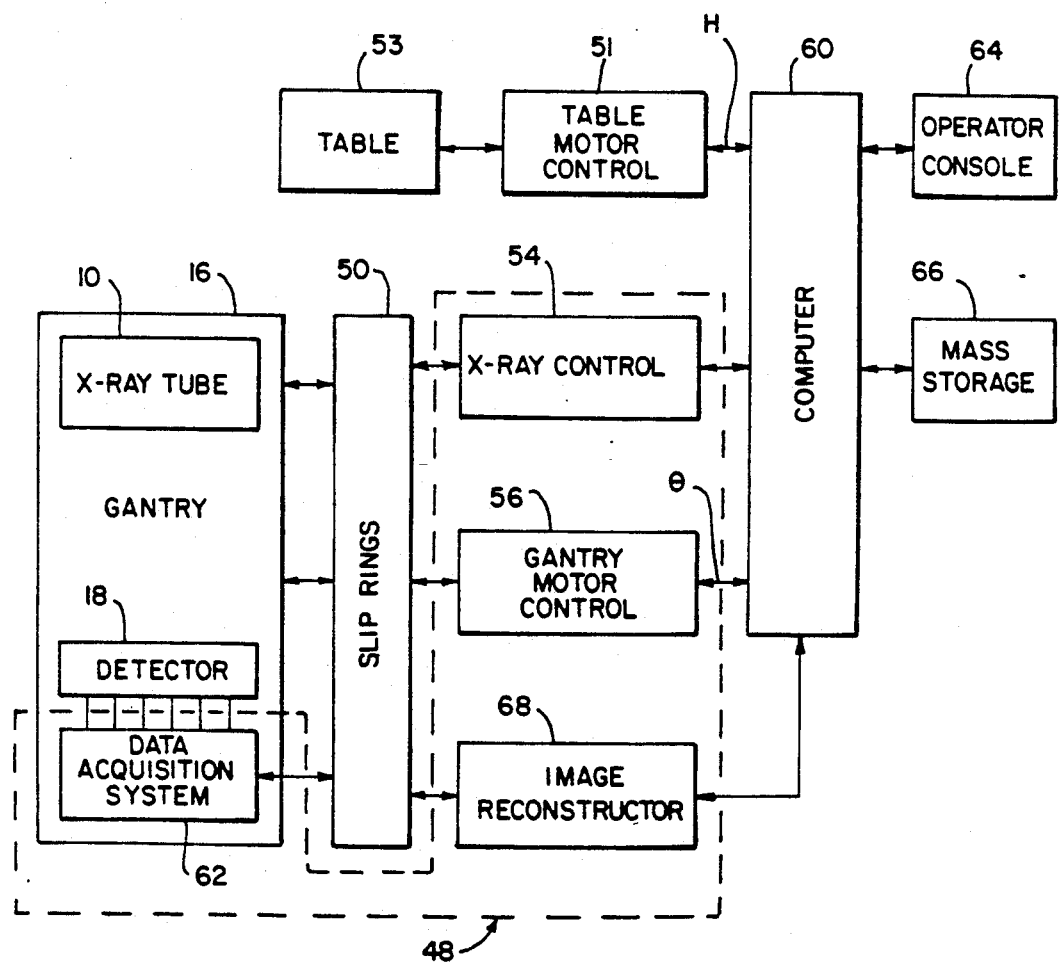
FIG. 2 is a block diagram of a CT control system associated with the gantry of FIG. 1 and useful for practicing the present invention.

Referring to FIG. 2, control circuitry for a CT imaging system suitable for use with the present invention includes a number of functional blocks 48. A data acquisition system 62 such as is generally understood in the art, is connected to the detector array 18 and comprises a sampling means (not shown) for sampling the signals from each of the channels 26. An analog to digital converter ("ADC") (not shown) converts the sampled analog signals from each sampled channel 26 to a digital value for processing by later circuitry. The ADC has a finite range and generally a trade-off must be established between the range of the intensity signals from each channel 26 which may be correctly digitized, and the resolution of the digitization process. Both considerations are important and a reasoned trade-off will necessarily allow certain situations where the range of the ADC will be exceeded. In the case of an over-range, the ADC will simply output its maximum value, regardless of how much greater the signal from the channel 26 is than this maximum value.

A radiotranslucent table 53 supports the patient 12 and the headholder 15, the latter which is typically fixed to the table 53. The table 53 may be moved through the image plane to align the slice of interest of the patient with the image plane, and may be raised or lowered to center the patient 12 within the opening of the gantry 16. The movement of the table is accomplished by motors (not shown) controlled by table motor control 51. The table motor control 51 also generates a value H indicating the height of table 53 with respect to the isocenter 19.

An x-ray control 54 provides power and timing signals to the x-ray source 10 with regard to the position of gantry 16 to acquire the projections. Gantry motor controller 56 controls the rotational speed and position of the gantry 16 and provides gantry angle information $\theta$ to the DAS 62 and the x-ray control 54 to permit accurate timing of the projections.

The image reconstructor 68 is a special purpose computer, such as an array processor, capable of very rapid parallel processing or "pipelining" as is necessary to produce images from the large amount of projection data. Array processors suitable for use as the image reconstructor 68 are commercially available from a variety of sources. The image reconstructor 68 receives the sampled and digitized signals from the channels 26 of the detector array via the DAS 62 to perform high speed image reconstruction according to methods known in the art.

A computer 60 coordinates the operation of the DAS 62, the table motor control, the x-ray control 54, and the gantry motor control 56 and works in conjunction with image reconstructor 68 to reconstruct tomographic images from the set of projections acquired by the scanning process. The computer 60 receives commands and scanning parameters via operator console 64 which is generally a CRT display and keyboard which allows the operator to enter parameters for the scan and to display the reconstructed slice images and other information from the computer 60. A mass storage device 66 provides a means for storing operating programs for the CT imaging system, as well as image data for future reference by the operator.

Each of the above elements is connected to its associated elements on the gantry 16 via slip rings 50 to permit continuous rotation of the gantry 16.

Operation of the Correction Process

Figure 4A:
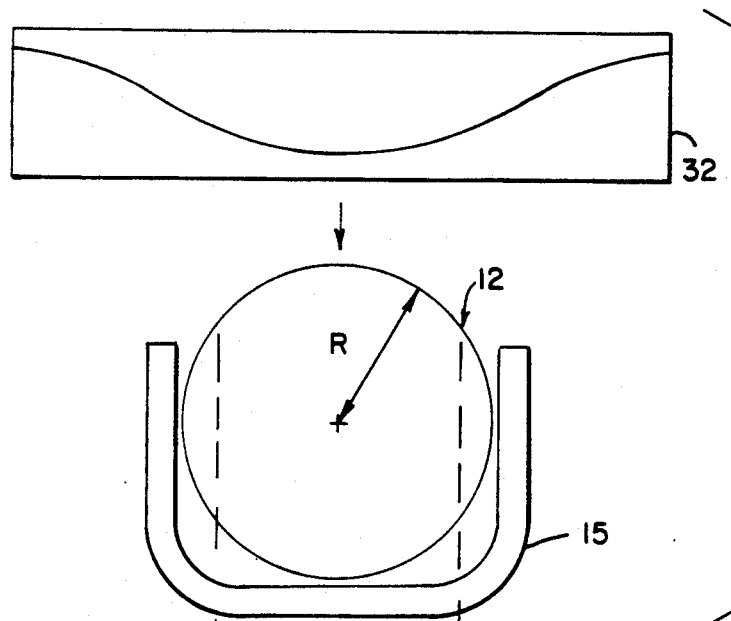
FIG. 4($a$)-($d$) are graphical representations of signals produced in the present invention by an example object held in the headholder of FIG. 1.

Referring now also to FIGS. 4(a) and (b), for a given position of gantry 16, the DAS 62 will produce a raw projection 36 comprised of the signals from each of the channels 26 of the detector array 18. This raw projection 36 has an in-range portion 22' corresponding to the in-range channels 22 and an over-range portion 21' corresponding to the over-range channels 21. For certain gantry angles, the over-range portion 21 may include some in-range channels associated with the headholder 15 which may provide sufficient attenuation to prevent over-ranging. The channel values of the over-range portion 21' are limited or clipped to the ADC maximum value 39, as has been described above, to produce clipped data 38.

Referring momentarily to FIG. 4(a), the in-range portion 22', in this example, corresponds to x-rays passing generally through the midsection of both the patient 12, and the bow tie filter 32 whereas the over-range portion 21' corresponds to x-rays intersecting only the edge and hence relatively little thickness of the patient 12 and the headholder 15 and the edge of the bow tie filter 32. The increasing attenuation of the bow tie filter 32 of the x-rays of the over-range portion 21', ultimately brings the raw projection signal 36 back in-range for channels at the extreme edge of the detector array 18. However, at the point where the x-rays of the fan beam 24 first pass on either side of the patient 12 without attenuation by the patient 12, the thickness of the bow tie filter 32 and the headholder 15 will often be insufficient to prevent clipping of the raw projection signal 36 at over-range portion 21'.

It will be understood that in situations other than that illustrated, the over-range portion 21' may be toward the mid-section of the detector array 18, for example if the imaged object 12 is substantially displaced about the isocenter 19. Thus the in-range portion 22' and over-range portion 21' may generally vary in their positions with respect to each other and the detector array 18.

Figure 4B:
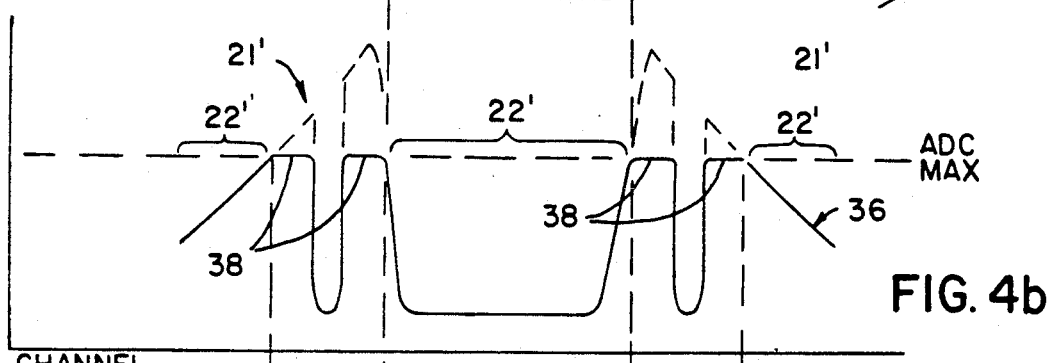
Figure 4C:
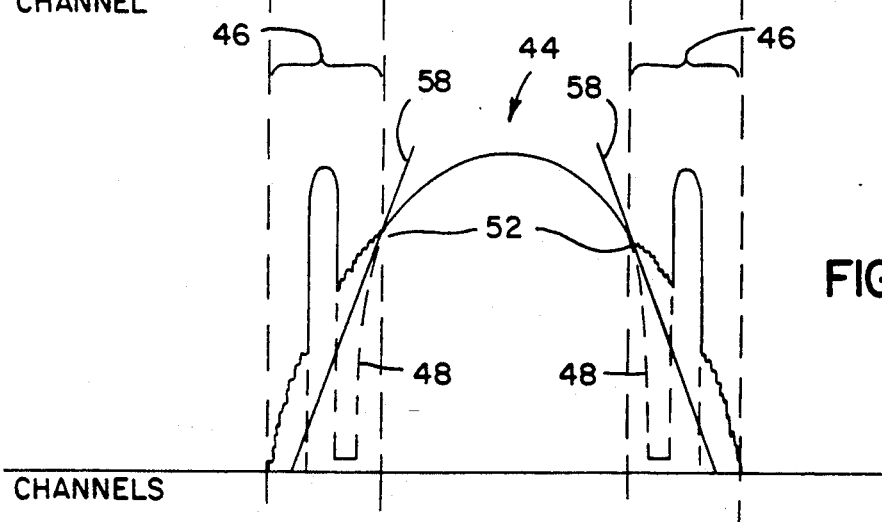
Figure 4D:
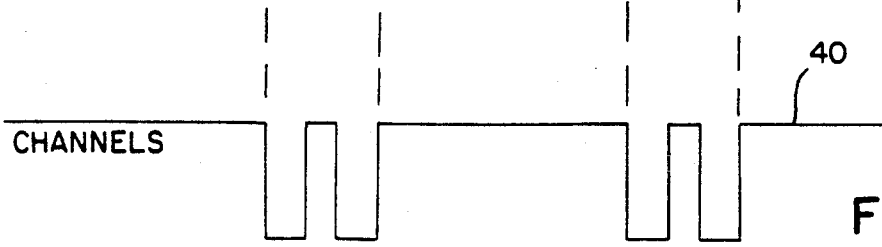

Referring now to FIGS. 4(b) and 4(d), the clipped data 38 of the raw projection 36 is readily identified as those portions of the raw projection 36 equal to the ADC maximum 39. Accordingly, an over-range mask 40 may be simply generated by comparing the raw projection 36 to the ADC maximum 39 and setting the over-range mask to "zero" for those points of the raw projection signal 36 substantially equal to the ADC maximum 39 and setting the over-range mask value to "one" for all other points.

Figure 3:
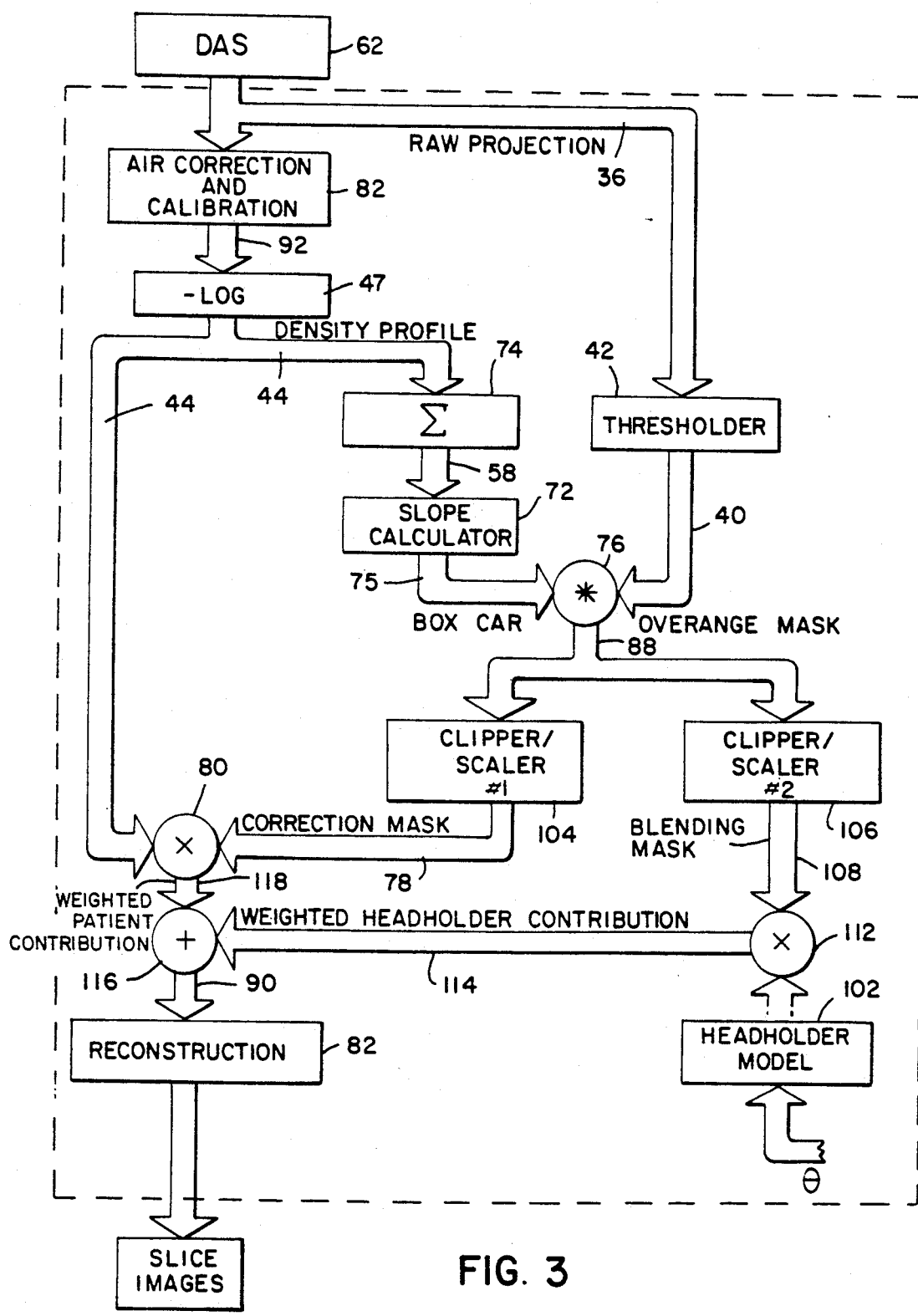
FIG. 3 is a block diagram showing the processing of the data acquired by the CT system according to the present invention.

Referring now to FIG. 3, this thresholding operation is represented by process block 42 which may be implemented by the array processor of the image reconstructor 68.

The raw projection 36 of FIG. 4(b) is next adjusted for the effects of the bow tie filter 32 and channel to channel variation in detector array 18 at an air correction step, indicated by process block 82, to produce corrected data 92. The correction of process block 82 is simply a point by point multiplication of the raw projection data 36 times a function, representing the compliment of the attenuation of the bow tie filter 32 and the channel to channel variation in the detector array 18, to effectively remove the contribution of the bow-tie filter 32 from the corrected data 92. This correction is followed by other calibration steps such as beam hardening correction, etc.

Referring to FIG. 4(c), the corrected data is next log adjusted by taking the negative of its logarithm to provide a density profile 44. Density in this case refers not to mass per unit volume but simply to the total amount of attenuating material of the imaged object 12 along the x-ray beam associated with a particular channel 26. The logarithmic correction is required because the attenuation of x-rays (or any radiation) by a medium is generally exponential, as illustrated by the following formula:

$$I = I_0 e^{-\int \mu(x,y) dl}$$

where $I_0$ is the x-ray intensity before it passes through the object having attenuation coefficients $\mu$ given over the x-y plane as $\mu(x,y)$, l is a distance along the x-ray path length and I is the x-ray intensity after the object.

The negating operation simply reflects the fact that decreasing intensity represents increasing density. This correction process is represented in FIG. 3 by process block 47.

Referring still to FIG. 4(c), the density profile 44 includes erroneous data in the areas 46, associated with the raw projection data of over-range portion 21' of FIG. 4(b). The correct data in these areas 46 are shown by the dotted lines 48 flanking the central unclipped data of the density profile 44, the latter unclipped data associated with the raw projection data of in-range portion 22' of FIG. 4(b).

Although the clipped channels 46 of the density profile 44 are at the edge of the density profile 44, they will create artifacts throughout the reconstructed image as a result of a convolution of the density profile 44 in the image reconstruction process as will be described. Convolution has the effect of spreading the contribution of each channel of data in the density profile 44, over the entire reconstructed image. Accordingly, it is necessary to correct even peripheral areas of clipped channels 46 prior to image reconstruction.

The present invention provides corrected data for clipped channels 46 by considering two factors. The first is the contribution of the patient 12 to the data of these clipped channels 46. The second is the contribution of the headholder 15. The present invention provides estimates of both of these contributions to generate substitute values for the data in the clipped channels 46 without reference to previous or later projections and without external measurements of the patient 12.

The Patient Contribution

The estimate of the contribution of the patient 12 is accomplished by employing a simplified model of the imaged object and fitting that model to the in-range channels for that projection. This process is the subject of co-pending application Ser. No. 07/800,197 filed on even date herewith and entitled: "Over-range Image Artifact Reduction in Tomographic Imaging" as now described.

The use of a model to calculate the patient contribution is based on the recognition that the slope of the data of the projections at the start of the areas of clipped data 46 will be directly proportional to the size of the object 12. This relationship may be illustrated in the following description where it will be assumed that the rays of the fan beam 24 are parallel rather than fan beam shaped for the purpose of clarity. The extension of this description to the case of a fan beam is a straightforward geometric transformation that will be understood to those of ordinary skill in the art. It will also be assumed that the imaged object 12 is a simplified geometric solid, preferably as a cylinder having radius R and a uniform attenuation coefficient $\mu$. This requirement will be relaxed later.

The density profile of the cylinder is described by the following equation:

$$p(x) = \begin{cases} 2\mu \sqrt{R^2 - x^2} & \text{if } x \leq R \\ 0 & \text{if } x > R \end{cases} \quad (1)$$

The term $2\sqrt{R^2 - x^2}$ is simply the path length along a chord through a cylinder of radius R as a function of its x-coordinate, the x-coordinate being measured along the detector array 18 with a value of x=0 at the center of the detector array 18. For the parallel case, the detector array 18 will be flat rather than curved.

For this cylinder, an over-range of a channel in the density profile 44 will occur for channels where the path length p(x) is less than a predetermined value C. The value C depends on the attenuation coefficient $\mu$ of the material of the cylinder, the strength of the x-ray source 10 after passing through the filter 30 and bow tie 32, and on the ADC maximum value 39. Taking the derivative of equation (1), and evaluating it at C provides the slope 58 where over-range starts:

$$\frac{dp(x)}{dx} = - \frac{\sqrt{R^2 - C^2}}{C} \text{ at } x = C \quad (2)$$

Since C will be much less than R for most clinical situations, equation (2) can be simplified to:

$$\frac{dp(x)}{dx} \approx \frac{R}{C} \quad (3)$$

Equation (3) indicates a linear relationship exists between the radius R of the imaged object 12 and the slope 58 of the density profile 44 at the starting point 52 of the clipped channels 46 (all shown in FIG. 4(c)) where over-range starts. The fact that this relationship is linear in this example greatly simplifies the estimation of the data of the clipped channels 46, it will be understood that other geometries of the imaged object 12 may be substituted for the cylindrical geometry if increased complexity of calculation performed above may be tolerated. Important, primarily, is that equation (3) suggests that slope 58 will be a function of R for a range of imaged objects 12, and as will be explained below, R may be deduced from the data of a single projection.

In order to take advantage of this functional dependance of the slope 58 of the data in region 46, on the value of the radius R, one must have an estimate of R. This estimate of R is obtained as follows: If, for the assumed parallel geometry, the attenuation of each volume element of the imaged object 12 in the imaging plane is represented by $\mu(x,y)$, a projection at a given gantry angle $\theta$ may be represented by the following equation:

$$P(\theta,t) = \int_{-\infty}^{\infty} \int_{-\infty}^{\infty} \mu(x,y)\delta(x\cos\theta + y\sin\theta - t)dxdy \quad (4)$$

where $\delta$ is the delta function and simply provides a notationally convenient way of generating the line integrals through $\mu(x,y)$ of the projection at gantry angle $\theta$, and t is a function of x and y related to the distance of each ray of the projection from the center 19, along a line normal to the path of the ray. The value t corresponds roughly to the position of the channels 26 within the detector array 18.

If we integrate this equation (4) with respect to the variable t, as would be done in practice by summing each value of the density profile 44 together, we obtain:

$$M = \int_{-\infty}^{\infty} \int_{-\infty}^{\infty} \int_{-\infty}^{\infty} \mu(x,y)\delta(x\cos\theta + y\sin\theta - t)dxdydt$$
$$= \int_{-\infty}^{\infty} \int_{-\infty}^{\infty} \mu(x,y)dxdy \quad (5)$$

Equation (5) is no longer a function of $\theta$ indicating that the sum of all the data in the density profile 44 depends solely on the attenuation coefficients $\mu$ of the object and is essentially independent of the gantry angle $\theta$ and thus of the particular projection acquired. Although this is not true for fan beam geometry, it has been determined that the variations in this integral for a fan beam case are small and thus the integral of equation (5) can be considered constant from projection to projection even for fan beams.

The total attenuation given in equation (5) may be used to estimate the value R. For a cylindrical imaged object the relationship is according to the following formula:

$$R = \sqrt{\frac{M}{\pi\mu}} \quad (6)$$

In the preferred embodiment, however, it is assumed only that the slope 58 is functionally related to the value of M and the functionality is determined empirically. Experiments have shown that the relationship between slope 58 and M is roughly linear in the regions of interest and therefore a simple constant of proportionality suffices. This constant of proportionality is obtained from measurements of actual patients. In practice different constants of proportionality are used for images of a patient's head as opposed to images of the patient's torso.

Referring to FIG. 3, this summation to determine M is shown by process block 74. The slope calculation of equation (3) is represented by process block 72 of FIG. 3.

Referring again to FIG. 4(c), the data of the density profile 44 at areas 46 may be conformed to the value of the slope 58 produced by the slope calculator 72 simply by searching the density profile 44 for the starting points 52 of the clipped channels 46. Working forward and backward from these starting points 52, the density of the starting points 52 may be progressively decreased according to the calculated slope 58 to generate new density values for the clipped channels 46.

Preferably, however, this correction process employs a method compatible with the pipelining capabilities of the array processor in the image reconstructor 68 as will be described below.

The Headholder Contribution

Figure 8:
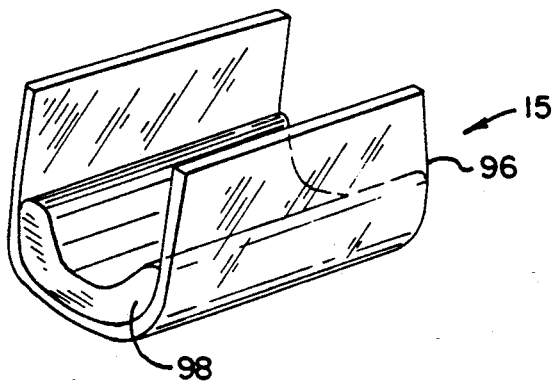
FIG. 8 is a perspective view of the headholder of FIG. 1.

Referring to FIG. 8, the headholder 15 comprises a U-shaped trough of Plexiglass 96 having a bottom foam pad 98 for cradling the patient's head.

The headholder 15 provides an invariant contribution to the density profiles 44 of a tomographic scan employing that particular headholder 15, in contrast with the variations expected in the particular patients 12. Thus, the headholder 15 may be precisely characterized without resorting to the approximations of a simplified geometric model as is done with the patient 12.

Figure 5:
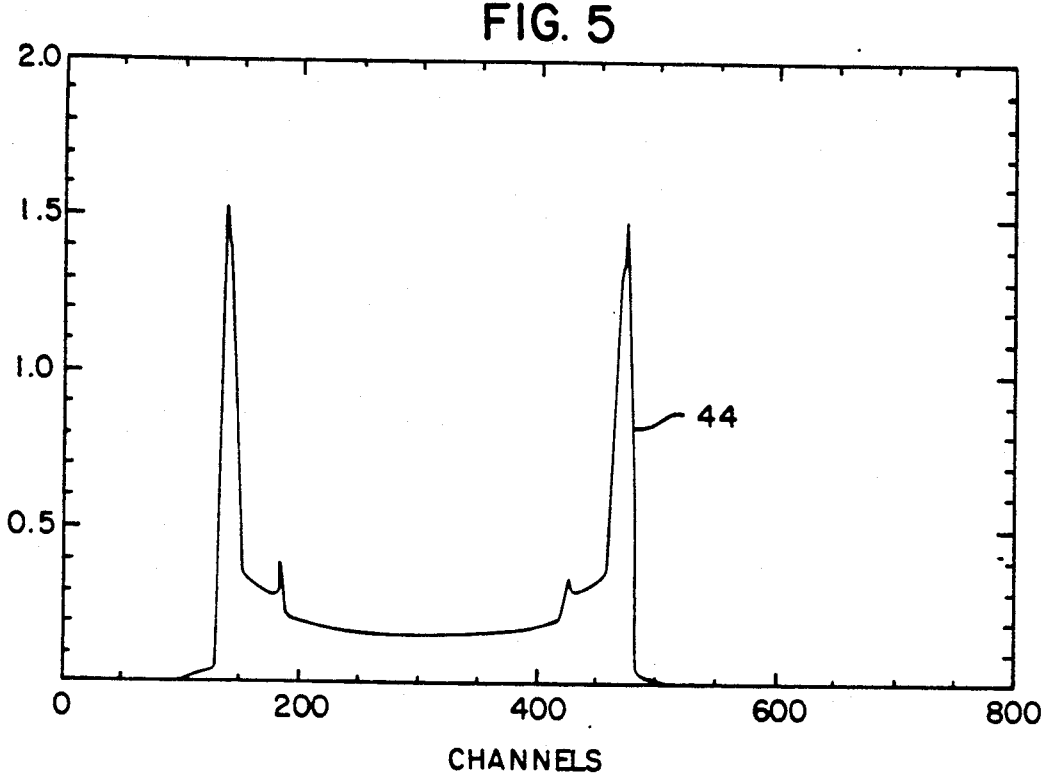
FIG. 5 is a graph showing the attenuation versus channel for the headholder of FIG. 1 at a gantry angle of 0 degrees.
Figure 6:
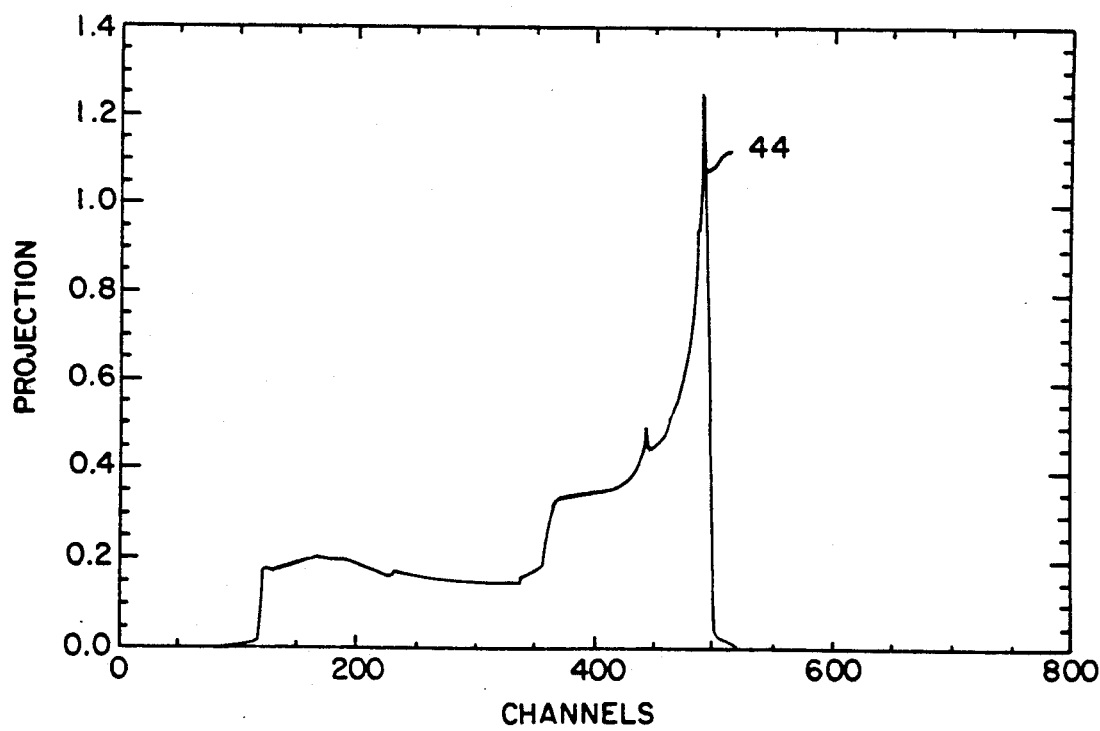
FIG. 6 is a figure similar to that of FIG. 5 showing the density profile of the headholder of FIG. 1 at 45 degrees.

Unfortunately, precise characterization of the headholder 15 is daunting. As shown in FIGS. 5 and 6, the density profiles 44 of the headholder 15 at various gantry angles show considerable variation. Even for a single density profiles 44 of the headholder 15, it is evident that the density profile 44 may not be approximated with a simple geometric model as was done with the patient 12. For example, the profile density 44 at a gantry angle of 0 degrees shown in FIG. 5, includes two relatively sharp spikes flanking a plateau. In contrast, the density profile 44 of the headholder 15 at the gantry angle of 45 degrees is completely asymmetric.

The discontinuous character of both density profiles 44 of FIGS. 5 and 6 suggests that accurately digitizing and sampling these density profiles 44 would require a large amount of stored data. Further, the variation in the density profile 44 of the headholder 15 with gantry angle requires that multiple density profiles 44 be stored, one for each gantry angle, if this density profile 44 data is to accessible for error correction in the same time frame as is the contribution of the patient 12 described above.

In order to avoid the burdensome amounts of data needed to store the density profiles 44 of the headholder 15, the present invention models the headholder 15 with a polynomial. Only the coefficients of the polynomial are stored for each gantry angle, substantially reducing the amount of stored data.

Given the general symmetry of the headholder, for example, as illustrated in the density profile 44 of FIG. 5, it has been determined that the use of a conventional polynomial employing a ramp basis function (e.g. $ax^0+bx^1+cx^2...$) would be inappropriate. Instead two customized basis functions were generated, one for characterizing the left hand portion of each density profile 44 and the other for characterizing the right hand portion of each density profile 44.

Figure 7:
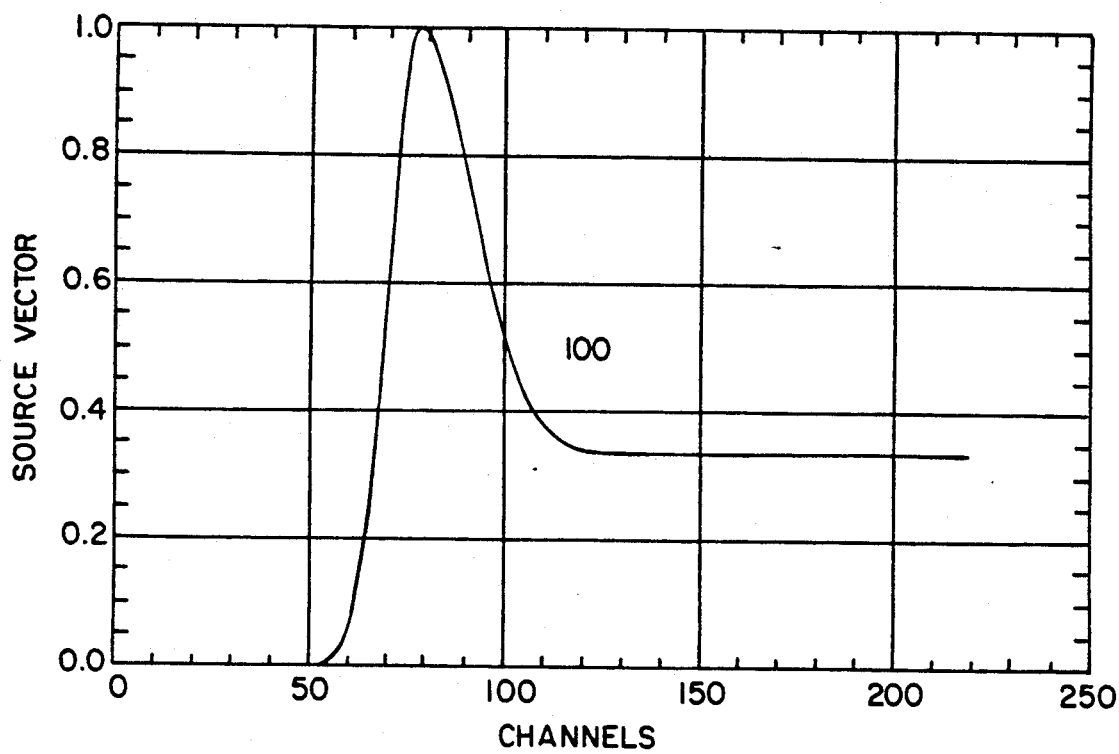
FIG. 7 is a graph of the basis function employed to model the projections shown in FIGS. 2 and 3 being a piece-wise Gaussian function.

Referring to FIG. 7, the first basis function 100 for decomposing the left hand portion of the density profile 44 of the headholder 15 is a piece-wise combination of Gaussian functions, normalized to values between 0 and 1 and reaching an asymptote of approximately 0.35 after first rising to a peak value of 1. This basis function was generated by inspection of the density profile 44 of the headholder 15 as shown in FIG. 5 but is suitable also for decomposing the density profile 44 shown in FIG. 6. The second basis function (not shown) is simply the left to right mirror image of the basis function shown in FIG. 7.

The headholder for a given gantry angle may be now characterized by the following equation.

$$\vec{H}(\theta) = \sum_{k=0}^{K} (\alpha_K(\theta)\vec{X}^k + \beta_K(\theta)\vec{Y}^k) \quad (7)$$

where $\theta$ is the gantry angle and $\vec{H}(\theta)$ is the density profile 44 of the headholder at that gantry angle and $\vec{X}^k$ and $\vec{Y}^k$ are the left and right basis functions respectively. The coefficients $\alpha_K(\theta)$ and $\beta_K(\theta)$ may be determined empirically by measuring a number of density profiles 44 of a headholder 15 without a patient 12.

The fitting of the coefficients to the actual projections entails dividing the density profiles 44 into a left and right hand side based on their total length and using the basis function 100 of FIG. 7 to characterize the left hand side and the basis function that is the mirror image of basis function 100 to characterize the right hand side. The polynomial (7) is then fit to the projections by least square fitting process known to those of ordinary skill in the art.

It has been determined that each density profile 44 of the headholder 15 at a given gantry angle can be represented by six coefficients (3 for the left hand side and 3 for the right hand side). Thus, the polynomial of equation (7) is limited to the second order.

The generated density profile 44 of the headholder 15 is next shifted with respect to the corresponding channels 26 of the detector array 18 (receiving the actual projection data from the patient 12) depending on the height H of the table 53, and hence the position of the actual headholder 15 with respect to the isocenter 19. As will be understood from the foregoing description, to those of ordinary skill in the art, the amount of such shifting will depend also on the gantry angle $\theta$ according to well known trigonometric formulas. This shifting of the generated density profile 44 of the headholder 15 aligns the generated density profile 44 with the actual position of the headholder 15 for each projection as attached to the table 53.

The process of generating the headholder projection used in the present invention from the gantry angle is shown as process block 102 of FIG. 3. Process block 103 requires that the gantry angle $\theta$ be provided. This gantry angle $\theta$ is used to look up in a lookup table (not shown) the necessary six coefficients which are then put into the equation 7 to generate the necessary density profile 44.

Combining the Patient and Headholder Contributions

It is necessary that the patient and headholder contributions to the data of areas 46, described above, be combined smoothly with the in-range channels to avoid introduction of further image artifacts during the reconstruction process. This may be accomplished by a weighting function used to weight the patient and headholder contributions as a function of channel prior to adding these two contributions together with the in-range channels.

In the present invention, the weighting and combining process is accomplished so as to be amenable to computation on the array processor 68. Accordingly, referring to FIG. 3, the slope calculated by the slope calculator 72 per equation (3), with respect to the contribution of the patient 12 described above, is used to produce a boxcar kernel 75. The box car kernel 75 is a binary signal having a values of 1 for a pulse of width $\tau$ chosen so that $\tau = 2$ slope.

Figure 9A:
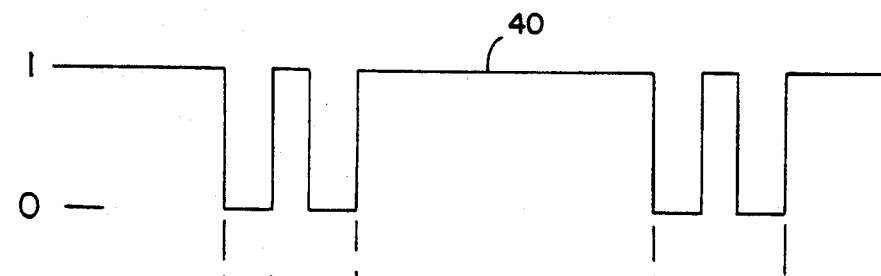
FIG. 9($a$)-($d$) are graphical representations of an over-range mask and signals generated therefrom for correcting the signals of FIG. 4($c$) per the present invention.

The box car kernel 75 and the over-range mask 40, the later generated by the thresholder 42 as described above, are convolved by convolver 76. The over-range mask 40 is shown if FIGS. 4(d) and 9(a).

Figure 9B:
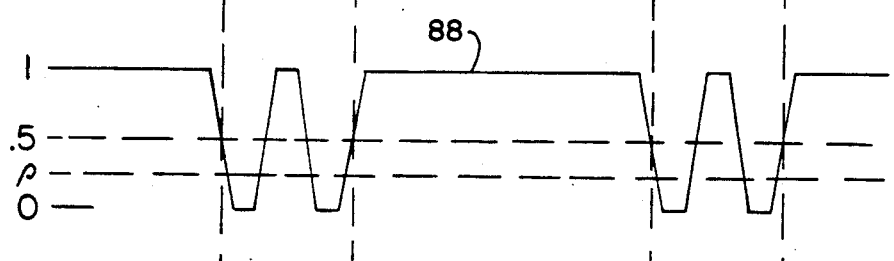

The result of this convolution 76 is a trapezoidal signal 88, shown in FIG. 9(b), having half the additional slope S needed to correct (through multiplication) the data of the clipped channels 46 to the slope 58 identified by the slope calculator 72. In particular, trapezoidal signal 88 has a peak value of one corresponding to some of the in-range channels of the density profile 44 and a slope of half of S, as calculated by the slope calculator 72 corresponding to some of the clipped channels of the density profile 44.

The trapezoidal signal 88 is next clipped and scaled by two clipper/scalers 104 and 106, in general having different clipping and scaling values as will be described, to produce a correction mask 78, used to correct the clipped channels 46 for the patient contribution, and a blending mask 108 used to blend the values from the headholder model 102 with the in-range channels.

Figure 9C:
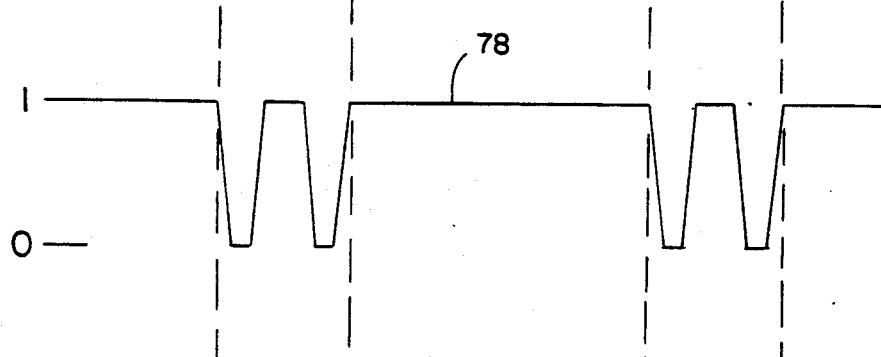

Referring now to FIGS. 3 and 9, the correction mask 78 is produced by the first clipper/scaler 104 which clips the trapezoidal signal 88, shown in FIG. 9(b) produced by the convolver 76 to values less than $\rho_1$, where $\rho_1$ is preferably equal to one-half, and then multiplies this clipped signal by $1/\rho_1$ producing the correction mask 78, shown in FIG. 9(c), having a value of one for all of the in-range channels of the density profile 44 and a slope equal to the slope S for the over-range channels.

The correction mask 78 is then multiplied by the density profile 44, as indicated by multiplier 80, so as to correct the data of the density profile 44 for the patient contribution to produce the desired slope 58 more closely approximating the true density profile 48 in a weighted patient contribution signal 118.

Figure 9D:
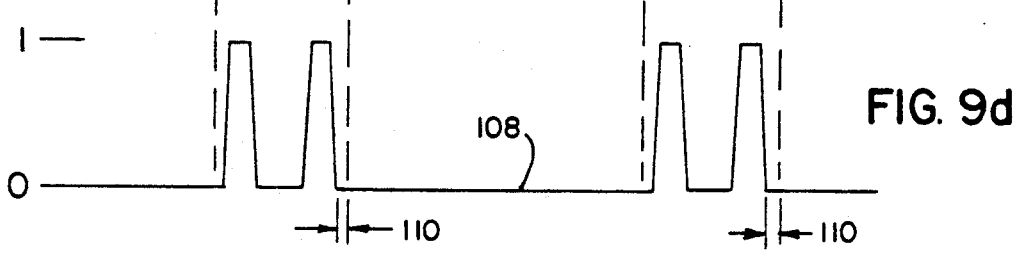

The blending mask 108 is produced by second clipper/scaler 106 which clips the trapezoidal signal 88, shown in FIG. 9(b) produced by the convolver 76 to values less than a predetermined value $\rho_2$, less than one half, and then subtracts these values from $\rho_2$ to the inverted signal and then multiplies this clipped and inverted signal by $1/\rho_2$ producing the blending mask 108, shown in FIG. 9(d). The blending mask 108 has a value of zero for all of the in-range channels of the density profile 44 and a portion 110, determined by $\rho$, of the clipped channels 46, the portion 110 approximating the area of the clipped channels 46 primarily affected by the contribution of the patient 12 and thus corrected by the correction mask 78. The value of ρ is determined empirically. The magnitude of the slope of the blending mask 108 is the same as that of S described above.

The blending mask 108 is used to weight the data from the headholder model 102, effectively zeroing the headholder model for the in-range channels, which implicitly include the actual headholder contribution, and giving increasing weight to the headholder model 102 for channels less likely to have attenuation by the patient 12. It is noted that the correction for the patient contribution provided by the correction mask 78 properly corrects for a constant headholder contribution in these areas as a result of the reliance on the slope 58 and starting points 52, the latter which are implicitly offset by the actual headholder contribution. The weighting of the headholder model 102 is provided by multiplier 112, shown in FIG. 3, which multiplies the blending mask 108 by the data for the headholder model 102 to produce a weighted headholder contribution 114.

The weighted headholder contribution 114 and the weighted patient contribution 118 are added together at summer 116 to produce a corrected projection 90.

Multiple projections 90 for multiple gantry angles are then reconstructed according to reconstruction methods well understood to those of ordinary skill in the art. One such algorithm is "filtered back projection" which involves a filtering of the projections 90, realized by multiplying the digitized transfer function of the filter times the Fourier transform of the projection 90. It will be recognized that this filtering is equivalent to a convolution of the projection 90, prior to its Fourier transform, with the inverse Fourier transform of the filter's spectral characteristic, and that such convolution effectively spreads errors in the projections 90 over the entire image. As mentioned, image artifacts caused by errors in the projections 90 at the periphery of the patient 12 may create image artifacts spreading throughout the image.

After the reconstruction, indicated by process block 82, slice images are available as indicated by process block 86.

It will be noted that the operations contained with the dotted line 68 of FIG. 3, representing those operations performed by the image reconstructor 68, are all suitable for pipeline processing. The requirements for executing a particular step in pipeline form is simply that the operation be capable of being performed on the inputted data of the sequential channels of the projection in their unsorted order without the need to search through or jump back into the channel data that has previously been examined. Because the thresholding of block 42 requires only a comparison of each channel of information against the ADC maximum 39, the thresholding process may be pipelined. The same is true with the summation of process block 74, and the convolution and multiplication and addition of process blocks 76, 80, 112 and 116. Likewise this is true for the clipping and scaling of process blocks 104 and 106.

The particular implementation of the correction process employing the calculated slope 58 is thus well suited for use in tomographic imaging systems which typically have such processors for performing the reconstruction of the images from the projection data.

Many modifications and variations of the preferred embodiment which will still be within the spirit and scope of the invention will be apparent to those of ordinary skill in the art. For example, the length and shape of the box car kernel used in the convolution may be varied to account for different models of the imaged object. Clearly the invention is not limited to use in correcting over-range data associated with headholders but may be used to correct for the attenuation of any invariant structure within the fan beam. In order to apprise the public of the various embodiments that may fall within the scope of the invention, the following claims are made:

We claim:

1. A compensation circuit for use in a tomographic scanner, the scanner employing an invariant structure adjacent to a body to be scanned and measuring a set of intensity values each related to the intensity of received radiation along one of a set of adjacent rays through both the scanned body and the invariant structure from a given gantry angle, the intensity values indicating the intensity of the received radiation up to a maximum, and not indicating the intensity of the received radiation above that maximum, the set of intensity values being combined with other sets of intensity values and reconstructed to produce an image, the circuit comprising:
   a threshold detector receiving the set of intensity values for identifying the set of intensity values an in-range intensity values corresponding to received radiation not above the maximum, and over-range intensity values corresponding to received radiation above the maximum;
   a model generator receiving the given gantry angle for producing estimated over-range intensity values corresponding to the intensity of radiation along rays passing through the invariant structure alone at the given gantry angle; and
   a combiner for combining the in-range intensity values with the estimated over-range intensity values prior to reconstruction of the intensity values into an image.

2. The compensation circuit of claim 1 wherein the threshold detector includes a comparator for comparing each intensity value to the maximum to identify only those intensity values equal to the maximum intensity value as over-range intensity values and the rest as in-range intensity values.

3. The compensation circuit of claim 1 wherein the model generator includes:
   a look-up table receiving the gantry angle for producing a predetermined set of coefficients; and
   a function generator receiving the coefficients from the look-up table for generating the estimated over-range intensity values from a polynomial employing the coefficients with a basis function.

4. The compensation circuit of claim 3 wherein the basis function is piece-wise Gaussian.

5. The compensation circuit of claim 3 wherein the combiner replaces a predetermined portion of the over-range intensity values with the estimated over-range values, the portion being those over-range values associated with rays at the outer edge of the set of adjacent rays.

6. The compensation circuit of claim 3 wherein the combiner comprises:
   a mask generator for producing a multipoint binary signal having a first value associated with each in-range intensity value and a value of zero associated with each over-range intensity value;
   a box car generator for producing a multipoint binary signal having a first value for a predetermined number of points and a value of zero for all remaining points;

a convolver for convolving signal from the mask generator signal with the signal from the box-car generator to produce a convolved signal;

a multiplier for multiplying the estimated over-range intensity signals by a corresponding value of the convolved signal to produce weighted estimated over-range intensity values; and a summer for adding the weighted estimated over-range values to the in-range intensity values.

7. The compensation circuit of claim 5 wherein the first value equals one and wherein the convolver clips the convolution of the signal from the mask generator signal and the signal from the box-car generator to values less than a predetermined blending value and then multiple this clipped signal by the inverse of the predetermined blending value to produce the convolved signal.

8. In a tomographic scanner measuring a set of intensity values each related to the intensity of received radiation along one of a set of adjacent rays through both an imaged object and an invariant structure from a given gantry angle, the invariant structure being adjacent to the body to be scanned, the intensity values indicating the intensity of the received radiation up to a maximum, and not indicating the intensity of the received radiation above that maximum, the set of intensity values being combined with other sets of intensity values and reconstructed to produce an image, a method of correcting for over-range comprising:

generating an over-range mask identifying the set of intensity values as in-range intensity values corresponding to received radiation not above the maximum, and over-range intensity values corresponding to received radiation above the maximum;

determining estimated over-range intensity values corresponding to the intensity of radiation along rays passing through the invariant structure along at the given gantry angle; and combining the in-range intensity values with the estimated over-range intensity values prior to reconstruction of the intensity values into an image.

* * * * *

UNITED STATES PATENT AND TRADEMARK OFFICE
CERTIFICATE OF CORRECTION

PATENT NO. : 5,225,980
DATED : July 6, 1993
INVENTOR(S) : Jiang Hsieh et al.

It is certified that error appears in the above-identified patent and that said Letters Patent is hereby corrected as shown below:

Col. 12, line 20  "2 slope" should be -- $\frac{2}{\text{slope}}$ --

Signed and Sealed this

Twenty-second Day of February, 1994

Attest:

BRUCE LEHMAN

*Attesting Officer*  *Commissioner of Patents and Trademarks*